United States Patent [19]

Woods

[11] 4,008,601
[45] Feb. 22, 1977

[54] FLUIDIC PARTIAL PRESSURE SENSOR

[75] Inventor: Robert L. Woods, Arlington, Tex.

[73] Assignee: The United States of America as represented by the Secretary of the Army, Washington, D.C.

[22] Filed: June 16, 1975

[21] Appl. No.: 587,474

[52] U.S. Cl. .................................................. 73/23
[51] Int. Cl.² ......................................... G01N 1/24
[58] Field of Search ........... 73/23, 196; 128/140 R, 128/142; 137/804

[56] References Cited
UNITED STATES PATENTS

| | | | |
|---|---|---|---|
| 1,633,352 | 6/1927 | Tate | 73/23 |
| 3,521,627 | 7/1970 | Murray | 128/142 |
| 3,756,068 | 9/1973 | Villarroel et al. | 73/23 |
| 3,771,348 | 11/1973 | Villarroel | 73/23 |
| 3,817,085 | 6/1974 | Stubbs | 73/23 |

Primary Examiner—Richard C. Queisser
Assistant Examiner—Stephen A. Kreitman
Attorney, Agent, or Firm—Nathan Edelberg; Robert P. Gibson; Saul Elbaum

[57] ABSTRACT

A fluidic partial pressure sensor for measuring the partial pressure of a gas constituent in a mixture relative to a reference gas. The pressure drop output of a fluidic bridge concentration sensor is connected to the aspirated input of a fluidic aspirator which is operated in its sonic or saturated region. By virtue thereof, the vacuum created in the aspirated input is directly proportional to the ambient pressure at the output of the aspirator. Since the ratio of the bridge pressure drop is therefore made constant, the output pressure of the bridge sensor is thereby directly proportional to the partial pressure of the gas constituent of interest.

2 Claims, 5 Drawing Figures

FLUIDIC PARTIAL PRESSURE SENSOR

RIGHTS OF THE GOVERNMENT

The invention described herein may be manufactured, used, and licensed by or for the United States Government for governmental purposes without the payment to me of any royalty thereon.

BACKGROUND OF THE INVENTION

1. Field of the Invention

This invention relates to fluidic devices and, more particularly, to fluidic apparatus which provides a direct measure of the partial pressure of a gas constituent in a mixture relative to a reference gas.

2. Description of the Prior Art

In an oxygen control system for aircraft pilots, it becomes necessary to control the oxygen delivery to the pilot as a function of altitude. That is, it is preferable to be able to provide the ground equivalent of oxygen to the pilot of an aircraft regardless of the altitude. In a physical sense, this requirement may be stated as that of providing a constant partial pressure of oxygen.

Prior art techniques utilized to control the amount of oxygen delivered to the pilot of an aircraft utilize concentration sensors which schedule the concentration of oxygen to be delivered as a function of the altitude of the aircraft. Such devices require a pair of measurements, i.e., concentration and altitude, and various computation equipment in order to schedule the right amount of oxygen to be admixed to the ambient air. Further, such devices are not generally responsive to situations involving varying ambient pressures.

It is therefore realized that it would be extremely advantageous to provide a device by means of which the partial pressure of a constituent gas within a mixture could be measured directly relative to a reference gas without the necessity for having an intermediate measurement of either concentration thereof or the altitude of the aircraft, or both.

Prior art United States patents in this field of which I am aware including the following U.S. Pat. Nos.: 2,283,750; 2,630,129; 2,998,009; 3,468,157; 3,556,098; 3,722,510; and 3,817,085. However, none of the foregoing patents provide a solution which approaches the simplicity, ruggedness, accuracy and versatility of the present invention to be described in more detail hereinafter.

SUMMARY OF THE INVENTION

It is therefore a primary object of the present invention to provide a fluidic apparatus which yields a direct indication of the partial pressure of a gas constituent in a mixture relative to a reference gas.

Another object of the present invention is to provide a direct-indicating fluidic partial pressure sensor which is mechanically rugged, has no moving parts, and is sensitive to changes in ambient pressure.

A still further object of the present invention is to provide a fluidic partial pressure sensor which utilizes a combination of well-known fluidic elements operable in a prescribed manner to yield an output pressure indication directly indicative of the partial pressure of a gas of interest.

The foregoing and other objects are attained in accordance with one aspect of the present invention through the provision of a fluidic apparatus which comprises a fluidic bridge concentration sensor which has a pair of input channels, one of which receives a reference gas, the other of which receives a gas mixture which includes the gas whose partial pressure is desired to be measured in the reference gas. The sensor further includes a reference output and a signal output. The pressure measurable at the signal output of the sensor is proportional to the volume concentration of the gas to be measured in the mixture and to the pressure drop across the input channels to the reference output. Means are connected to the reference output for ensuring that the pressure drop across the sensor is proportional to the ambient pressure, thereby providing an output signal across the sensor which is directly proportional to the partial pressure of the gas constituent of interest.

In accordance with a further aspect of the present invention, the fluidic means connected to the reference output of the sensor for ensuring the proportionality of the pressure drop to the ambient pressure comprises a fluidic aspirator which is operated in its sonic or saturated region. The aspirated inlet of the aspirator is connected to the reference output of the sensor and provides a vacuum pressure directly proportional to ambient, thereby yielding the desired result.

BRIEF DESCRIPTION OF THE DRAWINGS

Various objects, features and attendant advantages of the present invention will be more fully appreciated as the same becomes better understood from the following detailed description of the present invention when considered in connection with the accompanying drawings, in which.

DETAILED DESCRIPTION OF A PREFERRED EMBODIMENT

Figure 1:
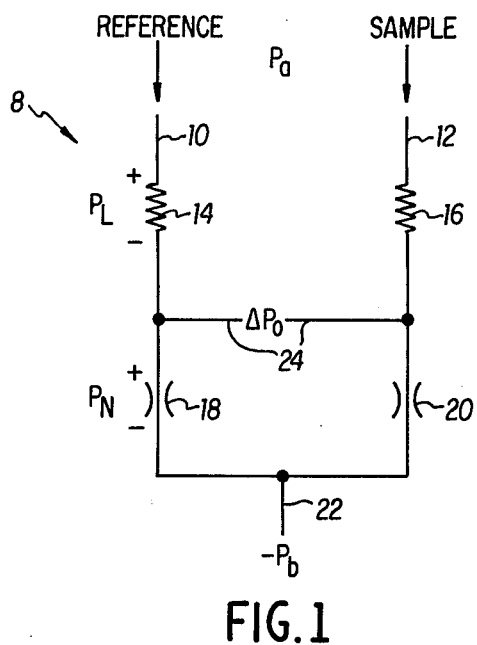
FIG. 1 is a schematic illustration of a preferred embodiment of a fluidic bridge gas concentration sensor which may be utilized in the fluidic apparatus of the present invention.

Referring now to the drawings, wherein like reference numerals and letters designate identical or corresponding parts throughout the several views, and more particularly to FIG. 1 thereof, there is depicted a preferred embodiment of a fluidic bridge gas concentration sensor utilizeable according to the present invention. The sensor 8 includes a pair of inputs 10 and 12 exposed to ambient pressure to which are respectively applied a reference gas at inlet 10 and a sample mixture at inlet 12. The sample mixture includes the gas whose partial pressure is desired to be measured, within the reference gas. For the sake of simplicity, it shall be assumed hereinafter that the gas whose pressure is desired to be measured is oxygen ($O_2$) in a reference of air.

The bridge 8 includes a pair of linear resistors 14 and 16 connected in the main input of the sensor, and a pair of non-linear resistors 18 and 20. One junction of non-linear resistors 18 and 20 is connected to a reference outlet channel 22 at which the sensor pressure drop $P_b$ is measured. The other junction of resistors 18 and 20 are respectively connected to resistors 14 and 16, the junction formed thereby serving as the output signal measurement port 24 across which the output pressure signal $\Delta P_o$ is measurable.

The output pressure $\Delta P_o$ may be measured by any well-known means, such as by an electronic pressure transducer, pressure gauge, monometer, or the like. Resistors 14, 16 18 and 20 should be selected to provide maximum gain through the sensor, other criteria also being taken into account. For a full discussion of such criteria, reference is made to Harry Diamond Laboratories' Report TM 73-9 entitled "Analog Flueric Gas Concentration Sensor" by F. Villarroel and R. L. Woods and dated June, 1973. A typical prior art fluidic bridge gas concentration sensor which may be utilized as sensor 8 is taught in Villaroel's U.S. Pat. No. 3,771,348, entitled: "Analog Flueric Gas Concentration Sensor."

As taught by the foregoing references, the output equation of the bridge gas concentration sensor 8 relates the output pressure $\Delta P_o$ to the volume concentration, the bridge pressure drop, and a pair of constants, as follows:

$$\Delta P_o = G P_b K_1 X \qquad (1)$$

wherein:

$\Delta P_o$ — bridge output pressure
$G$ = sensor gain constant
$P_b$ = bridge pressure drop
$K_1$ = gas sensitivity constant and
$X$ = volume concentration.

It should also be noted that the volume concentration $X$ is also equal to the ratio of the oxygen partial pressure $P_{o2}$ to the local ambient pressure $P_a$. Rewriting equation (1):

$$\Delta P_o = G P_b K_1 \frac{P_{o2}}{P_a} \qquad (2)$$

Thus, it is seen that the output pressure signal $\Delta P_o$ is proportional to a pair of constants $G$ and $K_1$. $G$ is the sensor gain constant which depends upon the particular parameters selected as sensor components, whereas $K_1$ is dependent upon the gases undergoing measurement as a function of viscosity, density, and other factors, but is constant for a particular mixture undergoing consideration.

It is seen by virtue of equation (2) that if one were able to obtain a vacuum pressure $P_b$ applied to bridge 8 which varied directly proportional to the ambient pressure $P_a$, then the output signal of the bridge $\Delta P_o$ would be directly proportional to the partial pressure of the oxygen in the mixture $P_{o2}$.

Figure 2:
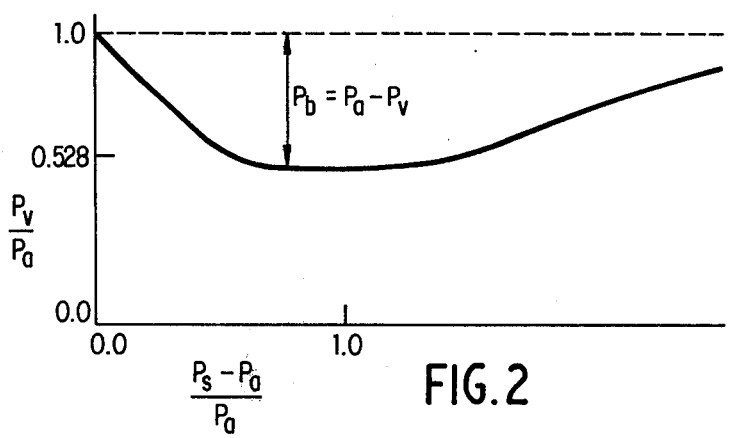
FIG. 2 is a graph showing the characteristics of the fluidic aspirator of FIG. 3, the latter also being utilizable in a preferred embodiment of the fluidic apparatus of the present invention.
Figure 3:
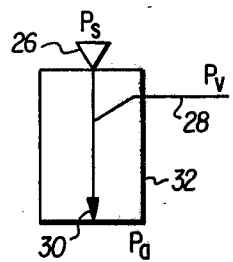

I have discovered that a fluidic aspirator utilized in its sonic or saturated region may be utilized to provide just such a vacuum pressure. FIG. 3 illustrates a well-known schematic of a fluidic aspirator 32 which includes a supply nozzle 26 into which is supplied fluid at a power supply pressure $P_s$, an outlet nozzle 30 which dumps to ambient pressure $P_a$, and an aspirated input 28 at a vacuum pressure $P_v$. FIG. 2 illustrates the characteristics of the aspirator 32 with a blocked load. It is seen that the region wherein $$0.5 < \frac{P_s - P_a}{P_a} < 2.0$$

the vacuum pressure $P_v$ is essentially constant. Since the ambient pressure $P_a$ is a function of altitude, in the aircraft-pilot preferred embodiment being described, the ambient pressure $P_a$, and thus the vacuum pressure $P_v$ will vary in proportion to one another.

Figure 5:
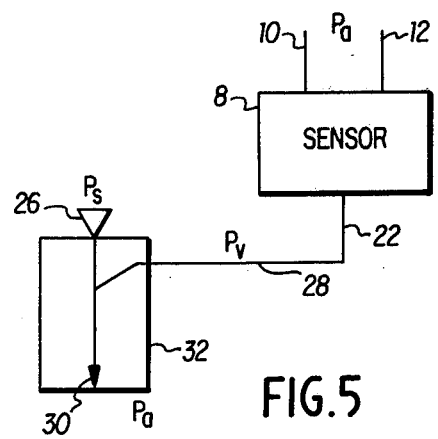

As depicted by the preferred embodiment in FIG. 5 of the present invention, the pressure vacuum $P_v$ of the aspirator 32, being itself proportional to ambient pressure $P_a$ when the aspirator is operated in its sonic region, can then be utilized to maintain a bridge pressure drop $P_b$ directly proportional to ambient pressure $P_a$, provided the aspirator inlet 28 is connected to the sensor reference outlet 22, as shown in FIG. 5. Mathematically speaking, $$\frac{P_b}{P_a} = 1.0 - \frac{P_r}{P_a} = \text{constant} = C_1 \qquad (3)$$

Thus
$$\Delta P_o = G C_1 K_1 P_{o2} \qquad (4)$$

or $\Delta p_o$ is directly proportional to partial pressure.

Figure 4:
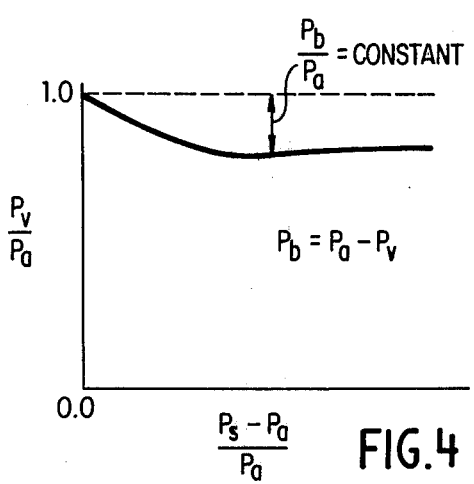
FIG. 4 is a graph illustrating the characteristics of the combination of the fluidic bridge gas concentration sensor and fluidic aspirator shown in FIG. 5, the latter of which comprises a preferred embodiment of the present invention.

The characteristics of the preferred embodiment are graphically depicted in FIG. 4 which basically depicts the aspirator characteristics when loaded with the concentration sensor 8, as shown in FIG. 5.

It was mentioned that the aspirator 32, itself a well-known component, is utilized in its sonic, choked flow, or saturated region. Physically, this implies that the power supply pressure $P_s$ fed in inlet nozzle 26, in trying to entrain flow from inlet 28, in its sonic condition chokes the mass flow therethrough which means that a constant vacuum is created above a certain inlet pressure.

It should be mentioned that the sensor gain constant $G$ is not entirely independent of ambient pressure; however, $G$ is substantially constant over a predictable range within which the apparatus of the present invention functions in the desired manner.

Obviously, numerous modifications and variation of the present invention are possible in light of the above teachings. It is therefore to be understood that within the scope of the appended claims the invention may be practiced otherwise than as specifically described herein.

I claim as my invention:

1. A method for obtaining a direct indication of partial pressure of a first gas in a reference gas, comprising the steps of:

supplying a fluidic bridge concentration sensor with said reference gas in a first input channel of said sensor and with a sample mixture comprising said first gas whose partial pressure is desired to be measured in said reference gas in a second input channel of said sensor;

exhausting said sample mixture and said reference gas through a reference output which ensures that said pressure drop across said fluidic bridge concentration is proportional to the ambient pressure by application of a vacuum, wherein said vacuum is achieved by means of a fluidic aspirator operated in its sonic region; and measuring the pressure difference across said input channels thereby obtaining a signal output which provides a pressure directly proportional to the partial pressure of said first gas in said reference gas.

2. A method for obtaining a direct indication of partial pressure of a first gas in a reference gas over varying pressures, comprising the steps of:

supplying a fluidic bridge concentration sensor with said reference gas in a first input channel of said sensor and with a sample mixture comprising said first gas whose partial pressure is desired to be measured in said reference gas in a second input channel of said sensor;

exhausting said sample mixture and said reference gas through a reference output which ensures that said pressure drop across said fluidic bridge concentration sensors is proportional to the ambient pressure by operating an aspirator in the choked flow condition in the region wherein $$0.5 < \frac{P_s - P_a}{P_a} < 2.0 \; ;$$

and measuring the pressure difference across said input channels thereby obtaining a signal output which provides a pressure directly proportional to the partial pressure of said first gas in said reference gas.

* * * * *